United States Patent [19]
Wittrock

[11] Patent Number: 6,017,217
[45] Date of Patent: Jan. 25, 2000

[54] HIGH PERFORMANCE DENTAL IMPRESSION TRAY STRUCTURE

[76] Inventor: Paul Wittrock, 1545 Flowerdale St., Simi Valley, Calif. 93063

[21] Appl. No.: 09/072,953

[22] Filed: May 5, 1998

Related U.S. Application Data

[60] Provisional application No. 60/080,646, Apr. 2, 1998.

[51] Int. Cl.[7] .......................................... A61C 9/00
[52] U.S. Cl. ................................. 433/37; 433/215
[58] Field of Search .................. 433/35, 37, 38, 433/41, 42, 43, 44, 45, 46, 47, 48, 80, 215, 216

[56] References Cited

U.S. PATENT DOCUMENTS

| | | | |
|---|---|---|---|
| 1,517,197 | 11/1924 | Cuttitta | 433/48 |
| 2,315,748 | 4/1943 | Thompson | 433/35 |
| 3,527,219 | 9/1970 | Greenberg | 433/215 |
| 4,810,294 | 3/1989 | Yagi et al. | 433/214 |
| 5,102,335 | 4/1992 | Getz | 433/38 |
| 5,336,086 | 8/1994 | Simmen et al. | 433/37 |
| 5,478,235 | 12/1995 | Schuldt et al. | 433/37 |
| 5,513,985 | 5/1996 | Robertson | 433/37 |

*Primary Examiner*—John J. Wilson
*Attorney, Agent, or Firm*—Louis J. Bachand

[57] ABSTRACT

Dental impression tray structure having a base and a trough supported by the base, the trough being adapted to carry a settable impression composition in conforming contact with teeth, the trough having a porous surface layer in open communication with the impression composition within the trough.

65 Claims, 2 Drawing Sheets

HIGH PERFORMANCE DENTAL IMPRESSION TRAY STRUCTURE

REFERENCE TO RELATED APPLICATIONS

This application claims the benefit of U.S. Provisional Application Serial No. 60/080,646 filed Apr. 2, 1998.

BACKGROUND OF THE INVENTION

1. Field of the Invention

This invention relates to dental impression trays, and more particularly to improved dental impression trays having a base and a trough for carrying dental impression composition into contact with teeth for making an impression, the tray having extended porous surfaces. In a particular aspect, the invention provides a dental impression tray capable of carrying a liquid such as water in contact with the dental impression composition so as to cool the impression composition. In other aspects, the invention provides a dental impression tray formed of sintered or fused individual metal or polymer bodies to have a desired degree of porosity, a roughened surface suitable for anchoring set impression composition for easy removal from the teeth, an occluded amount of liquid such as water useful for cooling a settable impression composition, the liquid suitably having a salt content for greater cooling capacity or medicaments for treating the mouth, a boss providing increased surface area in contact with the set impression composition, and/or a knife-carvable structure for ready adaptation to different size mouths or partial impression requirements. The porous surface and body as well in the invention dental impression tray is useful to absorb saliva in the mouth during the execution of dry field techniques.

2. Related Art

In dental practice, crowns, bridges and full or partial dentures are often fitted to patients to replace or repair the natural teeth. Each patient's mouth is unique in structural features so an effective crown or bridge to be comfortable must be closely fitted to the precise requirements of the individual. To ensure a close fit, an impression composition, comprising a natural or synthetic polymer that will set to a retained form, is applied to the areas to be replicated. The impression composition is necessarily impressionable and thus fluid. To carry the impression composition into the mouth, a dental impression tray is used. These trays comprise a base and a curvilinear trough generally sized and shaped to fit into the mouth and register with the patient's teeth. The impression material converts to a solid having in the negative the profile of the teeth and gums impressed into it. This impression is then used to form a stone model which is a positive of the teeth and gums. Then the bridge, crown or denture is fabricated using the stone model. Obviously, in all these steps errors in dimensions either from a faulty impression or a tearing of the set impression composition or a shrinkage or other distortion of the impression composition will adversely affect subsequent steps and result in a poor-fitting product.

The most exact dental impression composition is a hydrocolloid and it is the composition of choice when the highest quality impressions are desired. Usually, the hydrocolloid composition is applied to the teeth in the mouth in a heated, liquid form at about 110° F. The hydrocolloid is set in situ by cooling to a set gel in about 5–10 minutes. And thereafter removed. Metal dental impression trays are provided with internal passages having an inlet and outlet. Cooling water is circulated through passages to cool and set the hydrocolloid by heat transfer from the hydrocolloid to the cooled metal tray. This procedure requires a ready water supply at the dental chair and is inconvenient in having to hook up the inlet and outlet hoses and maintain them in place while the tray is in the patient's mouth for the duration of the setting period.

Traditionally, dental impression trays have been metal appliances that offer the benefits of reusability, although sterilization and more recently universal precautions are required for this type of reusable tray. Metal trays are smooth surfaced, as are all dental trays of which the applicant aware, to more readily release the set impression composition, and for cleanliness, but have undercuts to retain the set composition with the tray when the tray is removed from the mouth. Plastic trays have been proposed, also smooth surfaced and having undercuts to retain the set impression composition so that these trays have essentially been plastic editions of the common metal trays.

SUMMARY OF THE INVENTION

It is an object therefore of the present invention to provide an improved dental impression tray structure. It is another object to provide a dental tray that imbibes water and other liquids and holds them in occluded condition for impression composition cooling, to absorb saliva, to deliver medicaments into the mouth, or for other purposes. A further object is the provision of porous surfaces on a dental impression tray. Yet another object is to provide a dental tray having a through porosity from one surface to another that imbibes liquids and occludes them within the tray in open communication with compositions in contact with the impression tray surfaces for cooling and other purposes. Thus the objects of the invention include providing dental impression trays and, more particularly, porous dental impression trays having the capability:

1. To carry or occlude include cooling liquids for dental impression compositions that need to be cooled in the mouth to set;
2. To absorb saliva in the mouth when a dry field is desired;
3. To be knife-trimmed in the dental operatory to suit the individual patient's mouth or specific procedure such as a partial impression;
4. To carry or occlude medicaments for dental administration;
5. To incorporate medicament and other salts for activation upon liquid infusion to create a medicament liquid and/or have a negative heat of solution such that increased rates of impression composition cooling occur;
6. To surface anchor the impression composition in the set state to ease removal of the set impression composition from the mouth; and,
7. To increase the surface anchoring area for the impression material by having a boss within the tray to increase the available surface area.

These and other objects of the invention are realized in a dental impression tray structure having a base and a trough supported by the base, the trough being adapted to carry a settable impression composition in conforming contact with teeth, the trough having a porous surface layer in open communication with the impression composition within the trough. Typically, the structure base and trough comprise porous masses having a porosity such that water will drip therethrough when the base and trough are water-saturated but not before water-saturation.

In this and like embodiments, typically, the trough surface layer comprises a plurality of individual bodies joined together in surface pore defining relation; the individual bodies comprise metal, the bodies being sintered together in surface pore-forming relation; or, the individual bodies comprises a fusible plastic, the bodies being joined together in surface pore-forming relation. In the case of fusible plastic bodies typically, these bodies comprise polymer of an olefinically unsaturated monomer.

Significantly, the invention dental impression tray structure of fusible plastic bodies has a construction permitting ad hoc shaping thereof to a particular patient's mouth or for a partial impression, in the dental operatory, by hand-carving with a knife, or other suitable tool.

The invention dental impression tray structure trough surface layer typically has a plurality of pores sized and shaped to receive set impression composition in anchoring relation.

The invention thus provides a dental impression composition set in a tooth replicating shape, the set composition having a plurality of surface projections shaped to anchor the composition onto a porous surface.

The invention further provides, in combination: The above dental impression tray structure and a settable dental impression composition.

In this and like embodiments, typically, the dental impression composition comprises a formable natural or synthetic polymer, such as an alginate or hydrocolloid composition, or a polysulfide, polyvinyl, polysiloxane, polyurethane or polyether synthetic polymer composition.

In a further embodiment, the invention provides a dental impression tray structure having a base and a trough supported by the base, the trough being adapted to carry a settable impression composition in conforming contact with teeth, the structure base and trough comprising porous masses constructed and arranged to occlude liquid in structure surface communicating relation.

In this and like embodiments typically there is hydrocolloid dental impression composition in the tray, and the liquid is water in the tray pores in heat exchange relation with the hydrocolloid; the water can have dispersed therein a salt with a negative heat of solution so as to increase heat exchange potential by further cooling the water, or the liquid can carry or comprise a medicament needed to be placed in continuing proximity to the teeth such as a bleaching solution.

When the tray is used dry it will absorb mouth moisture such as saliva, and the invention thus provides a dental impression tray structure as described, and saliva imbibed therein to dry a field within the mouth.

In a further embodiment, the invention provides a dental impression tray structure having a base and a curvilinear trough supported by the base, the trough being adapted to carry a settable impression composition in conforming contact with teeth, the trough having a porous surface layer in open communication with the impression composition, the trough porous surface layer containing a trough surface-modifying fluid.

In a further embodiment, the invention provides a dental impression tray structure having a base and a curvilinear trough supported by the base, the trough being adapted to carry a settable impression composition in intimate contact with teeth, the trough comprising a porous mass in surface open communication with the impression composition, the trough porous mass containing a heat exchange fluid adapted for cooling the settable impression composition in composition setting relation.

In this and like embodiments, typically, the trough porous mass comprises a plurality of individual bodies joined together in mass pore defining relation; the trough mass pores are sized to occlude water within the mass; the tray base also comprises a porous mass, the base and trough porous masses being in open communication; the tray base and trough are integrally formed of a common mass; the trough has a porous surface layer, the trough surface layer comprising a plurality of individual bodies joined together in surface pore defining relation; the surface layer pores are sized and shaped to receive set impression material in anchoring relation; the trough surface layer pores are sized to occlude water within the surface layer; the tray structure is adapted for bringing a heated, settable impression material into contact with teeth, the tray base and trough porous masses being constructed and arranged to occlude a sufficient volume of liquid to cool the impression material to a set condition within 10 minutes; the settable impression material can be a hydrocolloid dental impression material, or an alginate, polyether, polysulfide, or polyvinyl siloxane resin.

The invention further provides a dental impression tray structure having a base structure and a curvilinear trough supported by the base, the base and trough each comprising a mass of plural individual bodies of metal or plastic joined together in pore-defining relation, the trough being adapted to carry a settable impression composition in intimate contact with teeth, the trough having a porous surface in open communication with the impression composition.

In this and like embodiments, typically, the individual bodies comprise metal, the metal bodies being bonded together in pore-defining relation, e.g. glued or sintered together in tray base and trough mass defining relation, or the individual bodies comprise synthetic organic plastic, such as polyolefin plastic, such as polymers or copolymers of ethylene and propylene; the individual bodies being agglomerated together, e.g. sintered together, in porous tray base and trough defining relation, and including also a surfactant permeating the base and trough; the tray is adapted for bringing heated, settable impression material into contact with teeth in a quantity sufficient to make a dental impression, the porous tray base and trough being constructed and arranged to occlude a sufficient volume of water to cool the quantity of impression material, such as a hydrocolloid dental impression material to a set condition within 10 minutes; the tray porous base and trough are constructed and arranged to occlude a sufficient volume of room temperature water to cool the hydrocolloid dental impression material to a set condition sufficient for removal from the mouth within 5 minutes; the tray porous base and trough define a porous surface layer, the base and trough porous surface layer comprising a plurality of individual bodies joined together in surface pore defining relation; the surface layer pores are sized and shaped to receive set impression composition in anchoring relation against separation of set impression composition from the tray in the course of separating the set impression composition from the teeth; the tray porous base and trough comprise by volume not less than about 40% voids and the balance the individual bodies; or the tray porous base and trough comprise by volume not less than about 60% voids and the balance the individual bodies.

In a further embodiment, the invention provides a dental impression tray structure having a base comprising a generally laterally extended wall, and a curvilinear trough supported by the base and comprising a wall generally normal to the base, the trough being adapted to carry a settable impression composition in conformable contact with teeth, the base and trough each having surface layer pores sized and shaped to receive set impression composition in anchoring relation.

In this and like embodiments, the base wall defines a boss having its longitudinal axis normal to the base, the boss extending generally opposite to and spaced from the trough wall, the boss having surface layer pores sized and shaped to receive set impression material in anchoring relation; the boss comprises an axially disposed series of decreasing area steps, each successive step being offset by a riser from the preceding step, the risers and steps having surface layer pores for increased numbers of surface layer pores in the structure for anchoring the set impression material; and, the tray base, base boss, and trough are integrally formed of a common mass comprising a plurality of individual bodies joined together in porous mass defining relation.

In its method aspects the invention provides the method of cooling a heated, settable dental impression composition while in contact with teeth, including directly contacting the dental impression composition with a cooling liquid cooler than the dental impression composition for a time sufficient to set the dental impression composition, retaining the cooling liquid within a porous support for the direct contact with the dental impression composition, and supporting the dental impression composition in contact with the teeth with the porous support while the cooling liquid is in direct contact with the dental impression composition.

In this and like method embodiments, typically, there is also included maintaining at least about 40% voids by volume in the porous support, and filling the voids with cooling liquid; or preferably, maintaining at least 60% voids by volume in the porous support, and filling the voids with cooling liquid; selecting water as the cooling liquid; treating the porous support with a surfactant before retaining the cooling water therein; and, adding a salt with a negative heat of solution to the liquid in liquid temperature-lowering amount before contacting the mouth with the tray structure.

In a further method embodiment, the invention provides the method of treating the mouth with a medicament, including directly contacting the mouth with a medicament, and supporting the medicament in mouth-contacting relation with a porous dental impression tray structure comprising a porous mass.

The invention further provides the method of taking a dental impression, including loading a surface porous dental impression tray structure with settable dental impression composition, applying the loaded composition to teeth, and withdrawing the tray after the impression material has set while anchoring the set impression material in the tray surface pores.

The invention further provides the method of taking a dental impression, including retaining a quantity of cooling liquid in a minutely through-porous dental impression tray structure, loading a quantity a heated, settable dental impression material into the tray structure in direct contact with the cooling liquid, bringing the dental impression composition into contact with teeth while maintaining contact of the dental impression composition with the cooling liquid within the porous tray for a time sufficient to set the dental impression composition, and supporting the dental impression composition in contact with the teeth with the porous support. In this and like embodiments of the invention, typically, there is also included carving the tray structure to a size and shape particularly adapted to the impression to be taken; selecting a temperature and quantity of the cooling liquid within the porous dental impression tray that given the quantity and temperature of the impression material, the impression material will set within about 5 to 10 minutes; selecting a hydrocolloid impression material, and maintaining at least about 40% voids by volume in the porous support; maintaining at least 60% voids by volume in the porous support; selecting water as the cooling liquid; treating the porous support with a surfactant before retaining the cooling water therein; adding a salt having a negative heat of solution to the cooling water; and/or saturating the porous support voids with water before addition of the impression composition thereto.

The invention further provides the method of fabricating a dental impression tray, including confining a mass of individual bodies in a mold cavity of suitable shape, and shaping the mass under pressure sufficient to mold the mass into a molded dental impression tray having at least about 40% voids by volume in the tray and a minute through-porosity such that water will drip through the tray when the tray is saturated but not otherwise.

BRIEF DESCRIPTION OF THE DRAWINGS

The invention will be further described as to an illustrative embodiment in conjunction with the attached drawings in which.

DETAILED DESCRIPTION

The present product and method delivers a cooling agent to the dental impression composition, shaped for extensive surface to surface contact with the impression composition. The porous structure described herein provides the shape by retaining the cooling agent in a desired form through the imbibing of a liquid cooling agent into the interstices of a suitably formed and foraminous or porous mass, and in the case of a metal porous mass providing a cooling agent in the form of a cooler structure, comprising the metal bodies, as well as a liquid cooling agent. For effective cooling, the porous mass and the cooling liquid may be regarded as a couple with their cooling effect, separately, being additive when used together. In general, the relative thermal conductivity of the impression composition on the one hand and the dental impression tray on the other will vary with the materials of the tray with metal trays being of course more thermally conductive that plastic trays, especially porous plastic trays. More significant in obtaining the goals of the invention is the obtaining of a significant temperature differential between the impression composition and the mass of the tray and its cooling agency, such as water, e.g. 20 to 50° F. or more up to 60° F., and preferably about 40° F. as in the case of cooling a hydrocolloid impression composition from about 110–120° F. with tap water at about 70° F.

Figure 1:
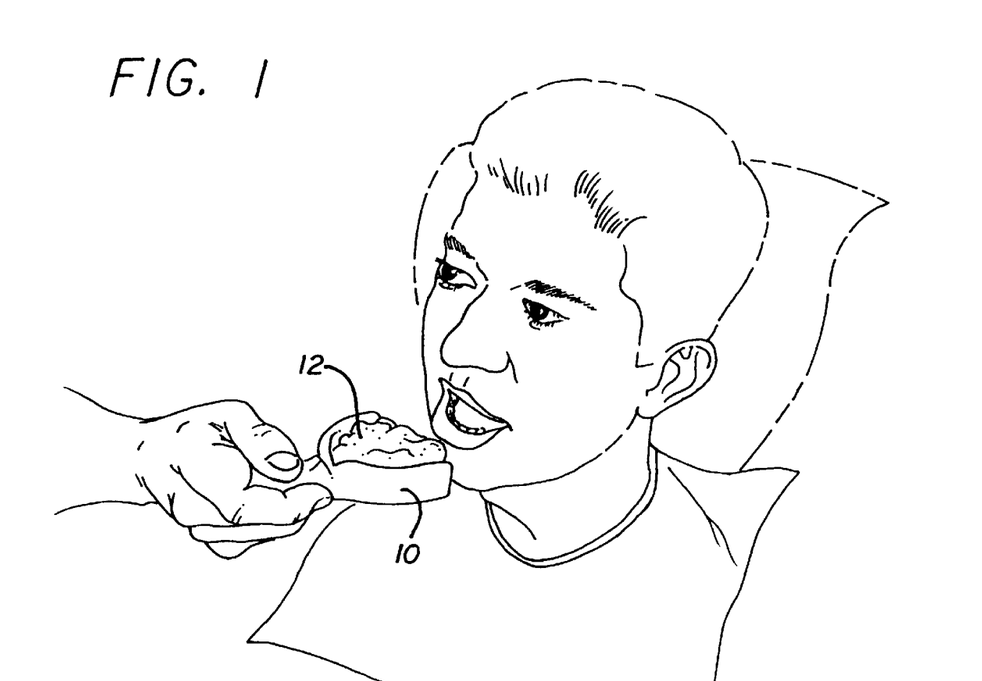
FIG. 1 is a pictorial view of a dental impression tray according to the invention as used in obtaining a dental impression.
Figure 2:
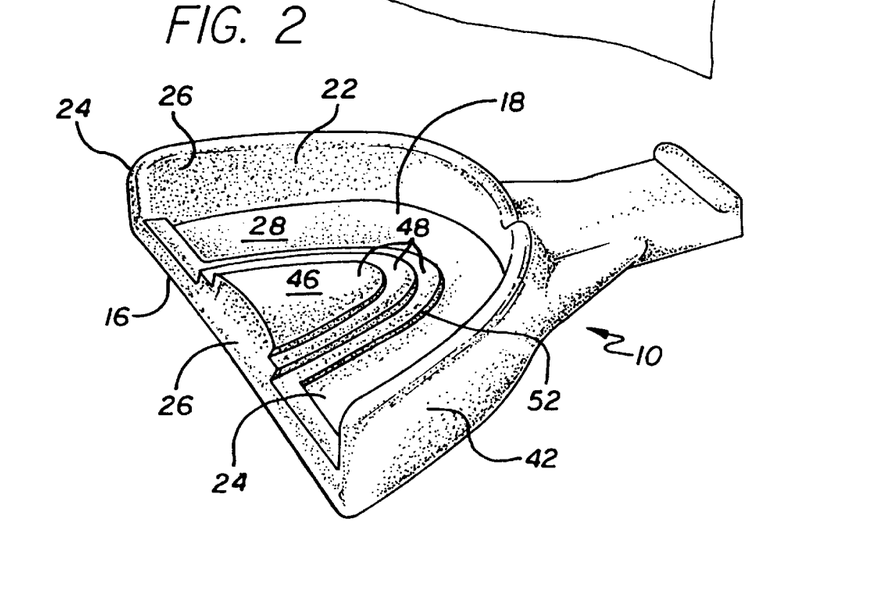
FIG. 2 is a perspective view of the invention dental impression tray.
Figure 3:
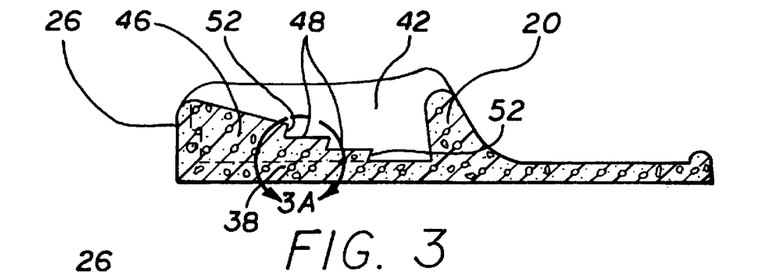
FIG. 3 is a view in vertical section of the dental impression tray.
Figures 3A, 4:
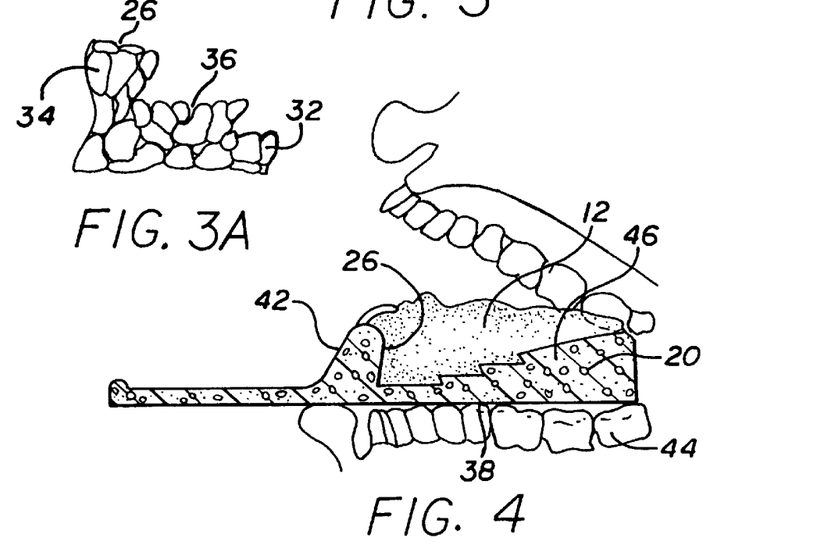
FIG. 3a is a view taken on line 3a in FIG. 3.
FIG. 4 is a view in vertical section of the dental impression tray, laded with impression composition and inserted into a mouth before taking an impression.
Figure 4A:
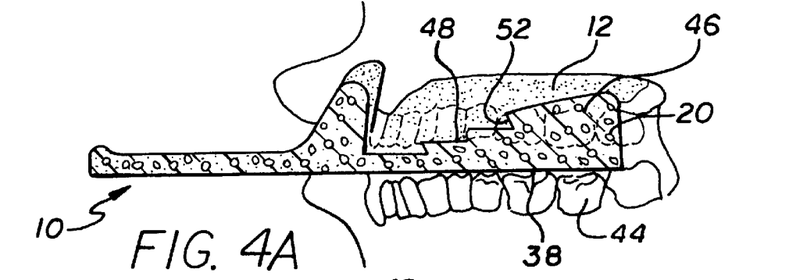
FIG. 4a is a view like FIG. 4 showing the jaw closed onto the dental impression tray and impression composition.

With reference now to the drawings, In FIGS. 1–4 a dental patient is being fitted with a dental tray 10 according to the invention, the tray being loaded with dental impression composition 12, suitably a hydrocolloid composition which is heated and which will cool within the mouth making an impression of the teeth and surrounding areas. In FIG. 2 and 3, the dental impression tray 10 before impression composition addition is shown to comprise a dental impression tray structure 14 having a base 16 and a trough 18 supported by the base. Trough 18 is adapted to carry the settable impression composition 12 in conforming contact with teeth, See FIGS. 4 and 4a, the trough having a porous surface layer 22 in open communication with the impression composition within the trough. Typically, the structure base 16 and trough 18 comprise porous masses 24 having pores 26 such that water 20 will drip therethrough when the base and trough are water-saturated but not before water-saturation. Before saturation, the water or other liquid cooling agent is occluded within the porous structure as water imbibition continues; after saturation the excess over the occluded water is released, or added water simply passes through the through-porous structure.

The surface layer 28 of the trough 18 comprises a plurality of individual bodies 32 joined together in surface pore 26 defining relation. The individual bodies 32 can comprise metal, the bodies being sintered together in surface pore-forming relation. See FIG. 5. Alternatively, the individual bodies 32 can comprise a plastic such as a fusible plastic or a thermoplastic plastic, particularly a polymer of an olefinically unsaturated monomer; or a thermoset plastic e.g. one in a fusible state or one treated to be fusible such as with a binder resin. In any case, the bodies 32 are joined together in surface pore 26-forming relation. Mixtures and combinations of different material types, different sizes and different degrees of sintering of individual bodies 32 can be employed provided the necessary porosity to retain sufficient cooling liquid for the above purposes of the invention is maintained.

It will be noted that the disclosed dental impression tray structure of fusible plastic bodies permits the ad hoc shaping thereof to a particular patient's mouth or for a partial impression, in the dental operatory, by hand-carving with a knife, drill-piece, or other suitable tool.

It will be further noted that the surface layer 28 porosity generated by the agglomeration of individual bodies 32, or in some cases by a leaching out of portions of the material volume, results in a surface effect of plural surface projections 34 numerous depressions, recesses, peaks and rises corresponding to the presence of innumerable individual bodies in close but not full contact such as defines pores 26. Surface layer 28 thus defines surface anchor sites 36 for reception of fluid dental impression composition, and retention of set dental impression composition. This retention feature is highly significant in dental practice. Once the dentist has made the impression it must be removed from the mouth, and from the teeth to which it tends to cling. The anchoring retention of the set impression composition 12 by the dental tray 10 ensures ready removal. In other dental trays undercuts were sometimes provided to assist in removal of the impression composition, but such hidden surfaces are possible sources of bacteria harboring and are desirably avoided.

Thus the present dental impression tray structure 14 base 16 comprises a generally laterally extended wall 38, and a curvilinear trough wall 42 supported by the base and normal to the base, the trough 18 being adapted by its wall 42 to carry the settable impression composition 12 in conformable contact with teeth 44, the base and trough each having surface layer pores 26 sized and shaped to receive set impression composition in anchoring relation.

The base wall 38 further defines a centrally located upstanding wall portion termed a boss 46. Boss 46 is generally pyramidal has its longitudinal axis normal to the base wall 38 and is provided to improve congruence with the mouth cavity, to increase the volume of porous tray structure 10, so as to include greater quantities of heat exchange liquid, and to increase the anchoring surfaces available. The boss 46 extends generally vertically, opposite to and is spaced from the vertically disposed trough wall 38. Boss 46 has surface layer pores 26 sized and shaped to receive set impression material in anchoring relation. Preferably, the boss 46 comprises an axially disposed series of decreasing area steps 48, each successive step being offset by a riser 52 from the preceding step, the risers and steps having surface layer pores 26 for increased numbers of surface layer pores in the structure for anchoring the set impression material.

In preferred modes of the invention dental impression tray structure 14, the tray base 16, base boss 46, and trough 18 are integrally formed of a common mass comprising a plurality of individual bodies 32 joined together in porous mass defining relation.

Thusfar, the description has focused on the use of surface layer porosity, e.g. a porosity in the first 20–30% of the tray structure 14 depth, referred to herein as the surface layer although it may be integral with the remainder of the tray structure. In a further embodiment, the invention provides a dental impression tray structure 14 having a base 16 and a trough 18 supported by the base, the trough being adapted to carry a settable impression composition in conforming contact with teeth, in which both the structure base and trough each comprise through-porous masses constructed and arranged to imbibe and occlude liquid in structure surface communicating relation. By surface communicating relation is meant such contact, direct or indirect that the temperature of the occluded liquid and the temperature of the setting impression composition temperatures are reciprocally affected, i.e. mutually moderated, by their contact.

In use of the full, through-and-through porosity embodiment of the invention, there is hydrocolloid dental impression composition in the tray, and the liquid is water 20 in the tray pores in heat exchange relation with the hydrocolloid. In some embodiments the water 20 has additives dispersed such as a medicament to treat the teeth or gums areas, for example, a surfactant, or a salt, particularly a salt with a negative heat of solution (i.e. water temperature is lowered by dissolving the salt) so as to increase heat exchange potential by further cooling the water. The added water or other heat exchange liquid also can carry or comprise a medicament needed to be placed in continuing proximity to the teeth, such as a tooth strengthening fluoride treatment or tooth whitening bleaching solution. In some embodiments, the salt or medicament or other desired additive such as a surfactant to aid permeation of the structure 14 by the liquids is pre-added to the porous tray structure 14 to be activated/solvated when the heat exchange, cooling liquid such as water 20 is incorporated into the porous mass that is tray structure 14. In other cases, the tray can be used to carry germicides to the underside of the impression composition.

It is to be noted, that the invention tray 10 has utility when not impregnated with liquid before use. Tray 10 can be used dry, for example, to absorb, imbibe and occlude mouth moisture such as saliva needed to be collected for dry field operations in the mouth.

Figure 5:
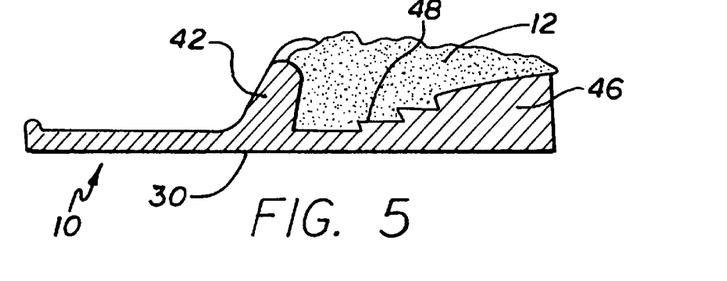
FIG. 5 is a view like FIG. 3 of a porous metal dental impression tray according to the invention.

With reference to FIG. 5, in certain embodiments, the individual bodies 32 comprise metal, such as stainless steel, the metal bodies being bonded together in pore-defining relation, e.g. glued or sintered together in tray base 16 and trough 18 mass defining relation. An added advantage of metal bodies 32 is that the resulting structure 14, being metal 30 will have its own cooling agency effect, added to the effect of the cooling agent liquid making a cooling couple.

In the case of either constituent of the porous tray 14, the base 16 and trough 18 are constructed and arranged to occlude a sufficient volume of water to cool the quantity of impression material, such as a hydrocolloid dental impression material to a set condition, preferably within 10 minutes, or more preferably occlude a sufficient volume of room temperature water to cool the hydrocolloid dental impression material to a set condition sufficient for removal from the mouth within 5 minutes, which is comparable to prior at cooling times using metal trays with water flow therethrough.

In general, the tray porous base 16 and trough 18 comprise by volume not less than about 40% voids and the balance the individual bodies 32, and preferably the tray porous base and trough comprise by volume not less than about 60% voids, the balance being the individual bodies. Typically, tray structures comprise olefin plastics, particularly polyethylene plastics. Porous plastics useful in the invention are available from vendors including Porex Technologies Corp. of Fairburn, Ga., and General Polymeric Corporation of Reading Pa. Porex fine polyethylene sheet No. X-4898 or No. X-4774 having an average mean pores size between 7 and 150 microns, and a porosity between 35 and 60% (35 to 60% voids by volume) have been found to be effective, with the higher porosity X-4774 product being preferred.

Speed of cooling impression compositions is an important factor in a dentist's acceptance of a particular tray, since the dentist cannot proceed while the impression is being cooled. Other factors, assuming speed between tray candidates is comparable is convenience. Conventional trays of nonporous metal having inlet and outlet ports for circulation of cooling water are fast but there is a considerable disadvantage in having to have water carrying tubing hooked to the tray in the patient's mouth.

The present trays obsolete the use of conventional trays with their cumbersome tubing. Typical cooling data obtained with the use of the invention tubingless porous tray structures show an improved rate of cooling and the achievement of hydrocolloid setting temperatures, e.g. 90° F. (down from 120° F.) in the same or less time than the conventional tray using recirculating water. The invention tray reaches all temperatures lower than the initial temperature faster and is specifically faster to the 4 minute mark just using tap water. Using chilled water, i.e. ice water, the invention tray achieved a temperature of 90° F. in the hydrocolloid in 25% less time, 3 minutes rather than 4 minutes, and had a faster rate of cooling at all time points. It would be quite expensive to plumb the dental operatory with ice water, but the invention tray can be simply dipped in ice water as easily as tap water, making these faster gel times readily available to the dentist.

The dental impression composition useful with the invention tray 10 can be any settable composition 12 capable of replicating teeth. Such compositions include, without limitation, formable natural or synthetic polymers, such as alginate or hydrocolloid compositions, or a polysulfide, polyvinyl, polysiloxane, polyurethane or polyether synthetic polymer composition.

In its method aspects, the invention includes cooling a heated, settable dental impression composition while in contact with teeth, by directly contacting the dental impression composition with a cooling agent such as a liquid, or a sintered metal mass, cooler than the dental impression composition for a time sufficient to set the dental impression composition, retaining the cooling liquid within a porous support for the direct contact with the dental impression composition, and supporting the dental impression composition in contact with the teeth with the porous support while the cooling agent liquid is in direct contact with the dental impression composition.

As in previous embodiments, the present method contemplates maintaining at least about 40% voids by volume in the porous support, and filling the voids with cooling liquid; or preferably, maintaining at least 60% voids by volume in the porous support, and filling the voids with cooling liquid; selecting water as the cooling liquid; treating the porous support with a surfactant before retaining the cooling water therein; and, adding a salt with a negative heat of solution to the liquid in liquid temperature-lowering amount before contacting the mouth with the tray structure.

The invention method of treating the mouth with a medicament includes directly contacting the mouth with a medicament, and supporting the medicament in mouth-contacting relation with a porous dental impression tray structure comprising a porous mass.

The invention method of taking a dental impression includes loading a surface porous dental impression tray structure with settable dental impression composition, applying the loaded composition to teeth, and withdrawing the tray after the impression material has set while anchoring the set impression material in the tray surface pores.

This method further includes retaining a quantity of cooling liquid in a minutely through-porous dental impression tray structure, loading a quantity a heated, settable dental impression material into the tray structure in direct contact with the cooling liquid, bringing the dental impression composition into contact with teeth while maintaining contact of the dental impression composition with the cooling liquid within the porous tray for a time sufficient to set the dental impression composition, and supporting the dental impression composition in contact with the teeth with the porous support.

The tray structure is suitably carved to a size and shape particularly adapted to the impression to be taken, a temperature and quantity of the cooling liquid within the porous dental impression tray is selected that given the quantity and temperature of the impression material, the impression material will set within about 5 to 10 minutes. A hydrocolloid impression material may be selected, and there can be maintained at least about 40% voids by volume in the porous support, or at least 60% voids by volume in the porous support. Water is preferably selected as the cooling liquid, and treating the porous support with a surfactant before retaining the cooling water therein, adding a salt having a negative heat of solution to the cooling water; and/or saturating the porous support voids with water before addition of the impression composition thereto are all aspects of the invention method.

The invention method of fabricating a dental impression tray includes confining a mass of individual bodies in a mold cavity of suitable shape, and shaping the mass under pressure sufficient to mold the mass into a molded dental impression tray having at least about 40% voids by volume in the tray and a minute through-porosity such that water will drip through the tray when the tray is saturated but not otherwise.

The foregoing objects are thus met.

I claim:

1. Dental impression tray structure having a base and a trough supported by the base, said trough being adapted to carry a settable impression composition in conforming contact with teeth, said trough comprising a wall normal to said base that encloses said impression composition and consisting essentially of a mass of individual bodies joined together in pore defining relation, said mass having a porous surface layer in open communication with said impression composition within said trough.

2. Dental impression tray structure according to claim 1, in which said structure base and trough comprise through-porous masses having a porosity such that water will drip therethrough when said base and trough are water-saturated but not before water-saturation.

3. Dental impression tray structure according to claim 1, in which said trough surface layer consists essentially of said individual bodies and is adapted to be in open communication with said impression material on three sides.

4. Dental impression tray structure according to claim 3, in which said individual bodies comprise metal, said bodies being sintered together in surface pore-forming relation.

5. Dental impression tray structure according to claim 3, in which said individual bodies comprise a fusible plastic, said bodies being joined together in surface pore-forming relation.

6. Dental impression tray structure according to claim 5, in which said fusible plastic bodies comprise polymer of an olefinically unsaturated monomer.

7. Dental impression tray structure according to claim 5, in which said impression tray of fusible plastic bodies has a construction permitting ad hoc shaping thereof in the dental operatory by hand-carving with a knife.

8. Dental impression tray structure according to claim 1, in which said trough surface layer has a plurality of pores sized and shaped to receive set impression composition in anchoring relation.

9. The dental impression tray structure according to claim 1, and further in combination with a settable dental impression composition.

10. The combination according to claim 9, in which said dental impression composition comprises a formable natural or synthetic polymer.

11. The combination according to claim 10, in which said impression composition comprises an alginate or hydrocolloid composition.

12. The combination according to claim 10, in which said dental impression composition comprises a polysulfide, polyvinyl, polysiloxane, polyurethane or polyether synthetic polymer.

13. Dental impression tray structure having a base and a trough with a vertical wall supported by the base, said trough being adapted to carry a settable impression composition in conforming contact with teeth, said structure base and trough vertical wall comprising porous masses constructed and arranged to occlude liquid in structure surface communicating relation.

14. The dental impression tray structure according to claim 13, and further in combination with a hydrocolloid dental impression composition in said tray, and water in said tray pores in heat exchange relation with said hydrocolloid.

15. The dental impression tray structure according to claim 13, and further in combination with water in which there is dispersed a salt with a negative heat of solution.

16. The dental impression tray structure according to claim 13, and further in combination with a liquid carried medicament.

17. The dental impression tray structure according to claim 13, and further in combination with saliva imbibed to dry a field within the mouth.

18. Dental impression tray structure having a base and a curvilinear trough supported by the base, said trough being adapted to carry a settable impression composition in conforming contact with teeth, said trough comprising a vertical wall extending normal to said base that encloses said impression material and consists essentially of a mass of individual bodies joined together in pore-defining relation, said trough having a porous surface layer in open communication with said impression composition, said trough porous surface layer containing a trough surface-modifying fluid before contact with said impression material.

19. Dental impression tray structure having a base and a curvilinear trough supported by the base, said trough being adapted to carry a settable impression composition in intimate contact with teeth, said trough comprising a porous mass in surface open communication with said impression composition, said trough porous mass containing a heat exchange fluid adapted for cooling said settable impression composition in composition setting relation.

20. Dental impression tray structure according to claim 19, in which said trough porous mass comprises a plurality of individual bodies joined together in mass pore defining relation.

21. Dental impression tray structure according to claim 20, in which said trough mass pores are sized to occlude water within said mass.

22. Dental impression tray structure according to claim 19, in which said tray base also comprises a porous mass, said base and trough porous masses being in open communication.

23. Dental impression tray structure according to claim 19, in which said tray base and trough are integrally formed of a common mass.

24. Dental impression tray structure according to claim 23, in which said trough has a porous surface layer, said trough surface layer comprising a plurality of individual bodies joined together in surface pore defining relation.

25. Dental impression tray structure according to claim 24, in which said surface layer pores are sized and shaped to receive set impression material in anchoring relation.

26. Dental impression tray structure according to claim 25, in which said trough surface layer pores are sized to occlude water within said surface layer.

27. Dental impression tray structure according to claim 26, said structure adapted for bringing a heated, settable impression material into contact with teeth, said tray base and trough porous masses being constructed and arranged to occlude a sufficient volume of liquid to cool said impression material to a set condition within 10 minutes.

28. Dental impression tray structure according to claim 27, in combination with a hydrocolloid dental impression material as said settable impression material.

29. Dental impression tray structure according to claim 25, in combination with an alginate, polyether, polysulfide, or polyvinyl siloxane resin as said settable impression material.

30. Dental impression tray structure having a base structure and a curvilinear trough comprising a vertical wall for enclosing dental impression material supported by the base, said base and trough each comprising a mass of plural individual bodies of metal or plastic joined together in pore-defining relation, said trough being adapted to carry a settable impression composition in intimate contact with teeth, said trough having a porous surface in open communication with said impression composition.

31. Dental impression tray structure according to claim 30, in which said individual bodies comprise metal, said metal bodies being bonded together in pore-defining relation.

32. Dental impression tray structure according to claim 30, in which said metal bodies are sintered together in tray base and trough mass defining relation.

33. Dental impression tray structure according to claim 30, in which said individual bodies comprise synthetic organic plastic.

34. Dental impression tray structure according to claim 33, in which said individual bodies comprise polyolefin plastic.

35. Dental impression tray structure according to claim 34, in which said polyolefin plastic comprises polymers or copolymers of ethylene and propylene.

36. Dental impression tray structure according to claim 30, said tray being adapted for bringing heated, settable impression material into contact with teeth in a quantity sufficient to make a dental impression, said porous tray base and trough being constructed and arranged to occlude a sufficient volume of water to cool said quantity of impression material to a set condition within 10 minutes.

37. Dental impression tray structure according to claim 36, in combination with a hydrocolloid dental impression material as said settable impression material.

38. Dental impression tray structure according to claim 37, in which said tray porous base and trough are constructed and arranged to occlude a sufficient volume of room temperature water to cool said hydrocolloid dental impression material to a set condition sufficient for removal from the mouth within 5 minutes.

39. Dental impression tray structure according to claim 38, in which said tray porous base and trough define a porous surface layer, said base and trough porous surface layer comprising a plurality of individual bodies joined together in surface pore defining relation.

40. Dental impression tray structure according to claim 39, in which said surface layer pores are sized and shaped to receive set impression composition in anchoring relation against separation of set impression composition from the tray in the course of separating the set impression composition from the teeth.

41. Dental impression tray structure having a base structure and a curvilinear trough supported by the base, said base and trough each comprising a mass of plural individual bodies of metal or plastic joined together in pore-defining relation, said trough being adapted to carry a settable impression composition in intimate contact with teeth, said trough having a porous surface in open communication with said impression composition, said individual bodies being agglomerated together in porous tray base and trough defining relation, and including also a surfactant permeating said base and trough.

42. Dental impression tray structure according to claim 41, in which said individual bodies are sintered together.

43. Dental impression tray structure having a base structure and a curvilinear trough supported by the base, said base and trough each comprising a mass of plural individual bodies of metal or plastic joined together in pore-defining relation, said trough being adapted to carry a settable impression composition in intimate contact with teeth, said trough having a porous surface in open communication with said impression composition said tray porous base and trough comprising by volume not less than about 40% voids and the balance said individual bodies.

44. Dental impression tray structure according to claim 43, in which said tray porous base and trough comprise by volume not less than about 60% voids and the balance said individual bodies.

45. Dental impression tray structure having a base comprising a generally laterally extended wall, and a curvilinear trough supported by the base and comprising a wall generally normal to said base, said trough being adapted to carry a settable impression composition in conformable contact with teeth, said base and trough each comprising porous masses and having therefrom surface layer pores sized and shaped to receive set impression composition in anchoring relation.

46. Dental impression tray structure according to claim 45, in which said base wall defines a boss having its longitudinal axis normal to said base, said boss extending generally opposite to and spaced from said trough wall, said boss having surface layer pores sized and shaped to receive set impression material in anchoring relation.

47. Dental impression material tray structure having a base comprising a generally laterally extended wall, and a curvilinear trough supported by the base and comprising a wall generally normal to said base, said trough being adapted to carry a settable impression composition in conformable contact with teeth, said base and trough each comprising porous masses and having therefrom surface layer pores sized and shaped to receive set impression composition in anchoring relation, said base wall defines a boss having its longitudinal axis normal to said base, said boss extending generally opposite to and spaced from said trough wall, said boss having surface layer pores sized and shaped to receive set impression material in anchoring relation, said boss comprising an axially disposed series of decreasing area steps, each successive step being offset by a riser from the preceding step, said risers having surface layer pores for increased numbers of surface layer pores in said structure for anchoring said set impression material.

48. Dental impression tray according to claim 47, in which said tray base, base boss, and trough are integrally formed of a common mass comprising a plurality of individual bodies joined together in porous mass defining relation.

49. The method of cooling a heated, settable dental impression composition while in contact with teeth, including directly contacting said dental impression composition with a cooling liquid cooler than said dental impression composition for a time sufficient to set said dental impression composition, retaining said cooling liquid within a porous support for said direct contact with said dental impression composition, and supporting said dental impression composition in contact with said teeth with said porous support while said cooling liquid is in direct contact with said dental impression composition.

50. The method according to claim 49, including also maintaining at least about 40% voids by volume in said porous support, and filling said voids with cooling liquid.

51. The method according to claim 50, including also maintaining at least 60% voids by volume in said porous support, and filling said voids with cooling liquid.

52. The method according to claim 49, including also selecting water as said cooling liquid.

53. The method according to claim 52, including also treating said porous support with a surfactant before retaining said cooling water therein.

54. The method according to claim 52, including also adding a salt with a negative heat of solution to said liquid in liquid temperature-lowering amount before contacting the mouth with said tray structure.

55. The method of taking a dental impression, including loading a surface porous dental impression tray structure with settable dental impression composition, said dental impression tray structure having a base and a trough supported by the base and comprising a wall normal to said base that encloses said impression composition and consisting essentially of a mass of individual bodies joined together in pore defining relation, said mass having a porous surface layer in open communication with said impression composition within said trough, applying said loaded composition to teeth, and withdrawing said tray after said impression material has set while anchoring said set impression material in said tray surface pores.

56. The method of taking a dental impression, including retaining a quantity of cooling liquid in a minutely through-porous dental impression tray structure, loading a quantity a heated, settable dental impression material into said tray structure in direct contact with said cooling liquid, bringing said dental impression composition into contact with teeth while maintaining contact of said dental impression composition with said cooling liquid within said porous tray for a time sufficient to set said dental impression composition, and supporting said dental impression composition in contact with said teeth with said porous support.

57. The method according to claim 56, including also carving said tray structure to a size and shape particularly adapted to the impression to be taken.

58. The method according to claim 56, including selecting a temperature and quantity of said cooling liquid within said porous dental impression tray that given the quantity and temperature of said impression material, said impression material will set within about 5 to 10 minutes.

59. The method according to claim 58, including also selecting a hydrocolloid impression material, and maintaining at least about 40% voids by volume in said porous support.

60. The method according to claim 59, including also maintaining at least 60% voids by volume in said porous support.

61. The method according to claim 58, including also selecting water as said cooling liquid.

62. The method according to claim 61, including also treating said porous. support with a surfactant before retaining said cooling water therein.

63. The method according to claim 61, including also adding a salt having a negative heat of solution to said cooling water.

64. The method according to claim 61, including also saturating said porous support voids with water before addition of said impression composition thereto.

65. The method of fabricating a dental impression tray, including confining a mass of individual bodies in a mold cavity of suitable shape, and shaping said mass under pressure sufficient to mold the mass into a molded dental impression tray having at least about 40% voids by volume in said tray and a minute through-porosity such that water will drip through said tray when the tray is saturated but not otherwise.

* * * * *